United States Patent [19]

Clark et al.

[11] Patent Number: 5,223,522
[45] Date of Patent: Jun. 29, 1993

[54] THIAZOLIDINEDIONE HYPOGLYCEMIC AGENTS

[75] Inventors: David A. Clark, East Lyme; Steven W. Goldstein, Mystic; Gerald F. Holland, Old Lyme; Bernard Hulin, Essex; James P. Rizzi, Waterford, all of Conn.

[73] Assignee: Pfizer Inc., New York, N.Y.

[21] Appl. No.: 857,039

[22] Filed: Mar. 24, 1992

Related U.S. Application Data

[62] Division of Ser. No. 679,898, Apr. 3, 1991, Pat. No. 5,120,754, which is a division of Ser. No. 566,436, Aug. 14, 1990, Pat. No. 5,061,717.

[51] Int. Cl.$^5$ .................. C07D 277/04; A61K 31/425
[52] U.S. Cl. ..................................... 514/369; 548/183; 546/280
[58] Field of Search .............. 546/280; 548/183; 514/369

[56] References Cited

U.S. PATENT DOCUMENTS

| | | | |
|---|---|---|---|
| 4,287,200 | 9/1981 | Kawamatsu et al. | 514/369 |
| 4,517,312 | 10/1986 | Schnur | 514/369 |
| 4,703,052 | 10/1987 | Eggler et al. | 514/337 |
| 4,725,610 | 2/1988 | Meguro et al. | 514/369 |
| 4,775,687 | 10/1988 | Meguro et al. | 514/369 |
| 5,120,754 | 6/1992 | Clark et al. | 514/369 |

OTHER PUBLICATIONS

Burger, Alfred, *Medicinal Chemistry*, vol. 3, 3rd Ed., pp. 64–80, Wiley-Interscience (1970).
Sohda et al., Chem. Pharm. Bull Japan, vol. 30, pp. 3580–3600 (1982) Chemical Abstracts 80:168259k (abstracting Japan Kokai 80-64586).

*Primary Examiner*—Alan L. Rotman
*Attorney, Agent, or Firm*—Peter C. Richardson; Gregg C. Benson; Mervin E. Brokke

[57] ABSTRACT

Hypoglycemic thiazolidine-2,4-dione derivatives of the formula

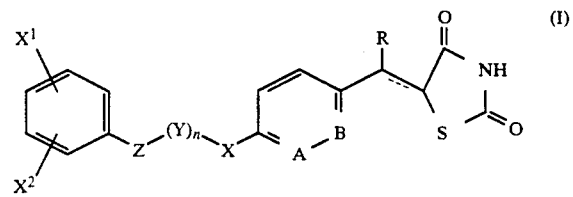

wherein
the dotted line represents a bond or no bond;
A and B are each independently CH;
X is S, SO, SO$_2$, CH$_2$, CHOH or CO;
n is 0 or 1;
Y is CHR$^1$ or NR$^2$, with the proviso that when n is 1 and Y is NR$^2$, X is SO$_2$ or CO;
Z is CHR$^3$, CH$_2$CH$_2$, CH=CH,

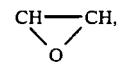

OCH$_2$, SCH$_2$, SOCH$_2$ or SO$_2$CH$_2$;
R, R$^1$, R$^2$ and R$^3$ are each independently hydrogen or methyl; and
X$^1$ and X$^2$ are each independently hydrogen, methyl, trifluoromethyl, phenyl, benzyl, hydroxy, methoxy, phenoxy, benzyloxy, bromo, chloro or fluoro;
a pharmaceutically-acceptable cationic salt thereof; or
a pharmaceutically-acceptable acid addition salt thereof.

6 Claims, No Drawings

THIAZOLIDINEDIONE HYPOGLYCEMIC AGENTS

This is a division of co-pending application Ser. No. 07/679,898, filed on Apr. 3, 1991 now U.S. Pat. No. 5,120,756, which is a division of application Ser. No. 07/566,436, now U.S. Pat. No. 5,061,717 filed on Aug. 14, 1990; as a request for U.S. examination of International Application No. PCT/US88,00744, filed Mar. 8, 1998.

BACKGROUND OF THE INVENTION

The present invention relates to certain compounds of the formula (I), depicted below, having utility as hypoglycemic and hypocholesterolemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque," which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendence toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

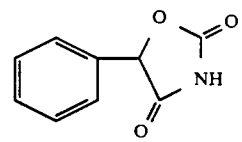

in which the phenyl ring is generally mono- or multi-substituted in the ortho/meta positions. Notably, with the exception of the 4-fluorophenyl analog, the para-substituted derivatives are either inactive or possess a low level of hypoglycemic activity.

Schnur, U.S. Pat. No. 4,342,771 discloses oxazolidinedione hypoglycemic agents of the formula

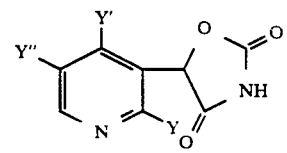

limited to compounds in which Y is hydrogen or alkoxy, Y' is hydrogen or alkyl and Y" is hydrogen or halo.

Schnur, U.S. Pat. No. 4,617,312 discloses hypoglycemic thiazolidinediones of the formula

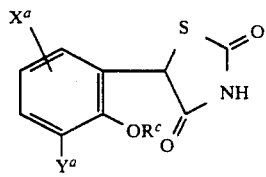

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen.

Kawamatsu et al., U.S. Pat. No. 4,340,605 disclose hypoglycemic compounds, also having plasma triglyceride lowering activity, of the formula

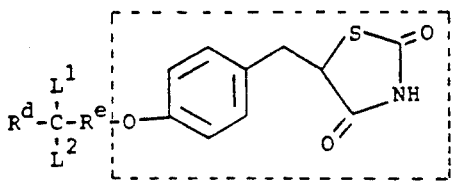

wherein $R^e$ is a bond or lower alkylene and when $R^d$ is optionally substituted phenyl, $L^1$ and $L^2$ may each be defined as hydrogen. Based on a lack of hypoglycemic and plasma triglyceride lowering activity of certain non-ether analogs, it has been suggested that the boxed portion of the structural formula, which includes the ether oxygen, represents an essential feature for useful activity in this series of compounds; Sohda et al., Chem. Pharm. Bull, Japan, vol. 30, pp. 3580–3600 (1982).

Eggler et al., U.S. Pat. No. 4,703,052, discloses hypoglycemic thiazolidinediones of the formula

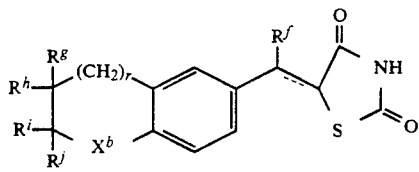

where the dotted line represents an optional bond, $R^f$ is H, methyl or ethyl, $X^b$ is O, S, SO, $SO_2$, $CH_2$, CO, CHOH or $NR^k$, $R^k$ is H or an acyl group and the numerous definitions of $R^g$, $R^h$, $R^i$ and $R^j$ include $R^g$, $R^h$ and $R^i$ as hydrogen or methyl and $R^j$ as optionally substituted phenyl, benzyl, phenethyl or styryl.

SUMMARY OF THE INVENTION

The present invention is directed to compounds having the formula

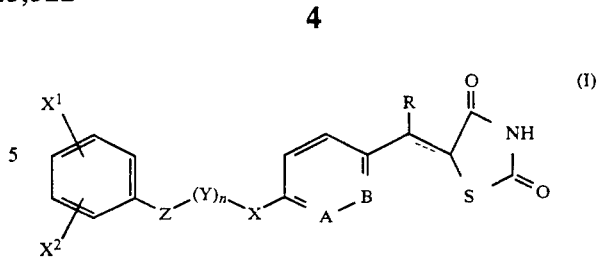

wherein
the dotted line represents a bond or no bond;
A and B are each independently CH or N, with the proviso that when A or B is N, the other is CH;
X is S, SO, $SO_2$, $CH_2$, CHOH or CO;
n is 0 or 1;
Y is $CHR^1$ or $NR^2$, with the proviso that when n is 1 and Y is $NR^2$, X is $SO_2$ or CO;
Z is $CHR^3$, $CH_2CH_2$, CH=CH, $$CH\!\!-\!\!CH,$$
$$\diagdown\!\!\diagup$$
$$O$$

$OCH_2$, $SCH_2$, $SOCH_2$ or $SO_2CH_2$;
R, $R^1$, $R^2$ and $R^3$ are each independently hydrogen or methyl; and
$X^1$ and $X^2$ are each independently hydrogen, methyl, trifluoromethyl, phenyl, benzyl, hydroxy, methoxy, phenoxy, benzyloxy, bromo, chloro or fluoro;
a pharmaceutically-acceptable cationic salt thereof; or
a pharmaceutically-acceptable acid addition salt thereof when A or B is N.

The preferred compounds are:
a) those wherein the dotted line represents no bond, A and B are each CH, X is CO, n is 0, R is hydrogen, Z is $CH_2CH_2$ or CH=CH and $X^2$ is hydrogen, particularly when $X^1$ is hydrogen, 2-methoxy, 4-benzyloxy or 4-phenyl;
b) those wherein A and B are each CH, X is S or $SO_2$, n is 0, R is hydrogen, Z is $CH_2CH_2$ and $X^2$ is hydrogen, particularly when $X^1$ is hydrogen or 4-chloro.

The expression "pharmaceutically-acceptable cationic salts" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salts" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hyperglycemic mammal or a hypercholesterolemic mammal which comprises a blood glucose lowering amount or a blood cholesterol lowering amount of a compound of formula (I) and a pharmaceutically-acceptable carrier. The invention further comprises a method of lowering blood glucose in a hyperglycemic mammal which comprises administering to said mammal a blood glucose lowering effective amount of a compound of formula (I); and a method of lowering blood cholesterol in a hypercholesterolemic mammal which comprises administering to said mammal a blood cholesterol lowering amount of a compound of the formula (I).

DETAILED DESCRIPTION OF THE PRESENT INVENTION

The compounds of the formula (I) of the present invention are readily prepared. Most generally, the compounds of the formula (I) wherein the dotted line represents a bond are prepared by reaction of thiazolidine-2,4-dione with an aldehyde or ketone of the formula

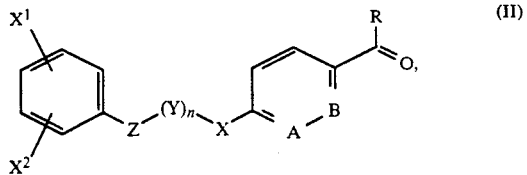

wherein A, B, R, X, $X^1$, $X^2$, Y, Z and n are as defined above. In this step, approximately equimolar amounts of the reactants are heated in the presence of a mild base to provide the olefin of formula (I) wherein the dotted line represents a bond. When X is C=O, the carbonyl group is preferably in protected form, e.g., as a ketal, preferably as the cyclic ketal formed with ethylene glycol. Examples of suitable mild bases for the above reaction include the alkali metal and alkaline earth salts of weak acids such as the $(C_1-C_{12})$alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. An especially preferred mild base is sodium acetate for reasons of economy and efficiency.

While this step may be carried out in the presence of a reaction-inert solvent, it is preferably carried out in the absence of solvent with excess sodium acetate as the base at a temperature which is sufficiently high to cause at least partial melting of the reaction mixture. A preferred such temperature is in the range of from 100° to 250° C., and especially preferred is a temperature of from 140° to 180° C. Usually a 10-25% molar excess of one of the two reactants is employed, in order to force the reaction to completion within a reasonable period of time, generally less than 1 or 2 hours. In the present instance, it is generally preferred to use the readily available thiazolidine-2,4-dione in excess.

As used here and elsewhere herein, the expression "reaction inert solvent" refers to a solvent which does not interact with starting materials, reagents, intermediates or products in a manner which adversely affects the yield of the desired product.

In a typical such reaction the aldehyde or ketone starting material (II) and thiazolidinedione are intimately mixed with a molar excess, preferably a 2-4 fold molar excess, of anhydrous sodium acetate and the mixture is heated at a temperature high enough to effect melting, generally about 140°-170° C., at which temperature the reaction is substantially complete in from about 5 to 60 minutes. The desired olefin of formula (I) wherein the dotted line represents a bond is then isolated, for example, by mixing with water and filtration, to obtain the crude product, which is purified, if desired, e.g., by crystallization or by standard chromatographic methods.

Particularly when R is hydrogen, an alternative preferred method is to couple a compound of the formula (II) with thiazolidine-2,4-dione in the presence of a catalytic amount of a secondary amine, preferably pyrrolidine or piperidine, usually about 0.05 to 0.20 molar equivalents, in a reaction-inert solvent such as a lower alkanol (e.g., methanol, ethanol, n-propanol, isopropanol). In this case temperature is not especially critical, but will generally be above room temperature but below 100° C. Reflux temperature of the lower alkanol solvent is particularly convenient.

These olefinic products are active hypoglycemic agents, but also serve as intermediates for preparation of the corresponding reduced compounds of formula (I) wherein the dotted line represents no bond. While the reduction of the above olefins may be carried out by employing a wide variety of reducing agents which are known to reduce carbon-to-carbon double bonds, the preferred methods employ hydrogen in the presence of a noble metal catalyst, zinc in acetic acid, or sodium amalgam or magnesium metal in methanol. When X is CO, hydrogenation over Pd/C in tetrahydrofuran under mild conditions is preferred.

When the reduction step is carried out employing hydrogen in the presence of a noble metal catalyst, a convenient method for carrying out this transformation is to stir or shake a solution of the olefinic compound of the formula (I) wherein the dotted line represents a bond in a reaction-inert solvent under an atmosphere of hydrogen, or hydrogen mixed with an inert diluent such as nitrogen, in the presence of a noble metal hydrogenation catalyst. Suitable solvents for this reaction are those which substantially dissolve the starting compound but which do not themselves suffer hydrogenation or hydrogenolysis. Examples of such solvents include ethers such as diethyl ether, tetrahydrofuran, dioxane and 1,2-dimethoxyethane; low molecular weight amides such an N,N-dimethylformamide, N-N-dimethylacetamide and N-methylpyrrolidone; and lower alkyl carboxylic acids such as formic, acetic, propionic and isobutyric acid. Especially preferred such solvents are tetrahydrofuran and glacial acetic acid.

Introduction of the hydrogen gas into the reaction medium is usually accomplished by carrying out the reaction in a sealed vessel containing the olefinic compound, solvent, catalyst and hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenation is generally run at a temperature of from about 0° to about 60° C., and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation; for example, palladium, platinum and rhodium. A palladium catalyst is preferred because such catalysts are not readily poisoned by sulfur. The catalyst is usually present in an amount from about 0.01 to about 25 weight-percent, and preferably from about 0.1 to about 10 weight-percent, based on the olefinic compound. It is often convenient to suspend the catalyst on an inert support; a particularly convenient catalyst is palladium suspended on an inert support such as carbon.

When in the olefinic compound X is carbonyl (or the protected ketal form thereof) or carbinol (CHOH), hydrogenation under more vigorous conditions will generally not only produce the compound of the formula (I) wherein the dotted line no longer represents a bond, but also wherein X is methylene.

When the hydrogenation of the methylene double bond (and when desired, other groups) is substantially complete, the desired product of formula (I) wherein the dotted line is no bond is then isolated by standard methods, e.g., the catalyst is recovered by filtration, the solvent evaporated and the product purified, if desired, by well known methods such as crystallization or by chromatography.

Ketal protecting groups are readily removed by conventional acid catalyzed hydrolysis, as exemplified below, to form those compounds of the formula (I) wherein X is C=O.

Another preferred method for reduction of the olefinic compounds of the formula (I) wherein the dotted line represents a bond is conventional sodium amalgam, usually at or about ambient temperature, as exemplified below. When X is CO, sodium amalgam will generally also reduce this group to CHOH.

Another preferred method for reducing the olefinic double bond when present in the compound of the formula (I) is zinc in acetic acid, particularly valuable when the side chain contains no group (e.g. ketonic carbonyl, sulfonyl or sulfonyl [other than sulfonamides]) which are generally susceptible to reduction with this reagent. Suitable conditions are an excess of zinc dust, e.g., up to a 10-fold molar excess in glacial acetic acid at about 80°–130° C., conveniently the reflux temperature of the reaction mixture at ambient pressure, as exemplified below.

Furthermore, those compounds wherein X is CHOH (carbinol) are also conveniently prepared by conventional sodium borohydride reduction of the corresponding compound wherein X is C=O. In the alternative, compounds wherein X is CO are also conveniently prepared by oxidation of those compounds wherein X is CHOH by means of the Jones oxidation.

Those compounds wherein X is SO or $SO_2$ (with Y as other than NR) or Z is $CH_2SO$ or $CH_2SO_2$ are preferably formed by suitable oxidation of the corresponding compounds where X is S or Z is $CH_2S$. When the sulfoxide is desired, the sulfide is preferably oxidized with at least one molar equivalent (usually a 2–3 fold molar excess) of sodium periodate in a reaction inert solvent such as aqueous methanol, generally at room temperature or below so as to avoid over oxidation. Alternatively, close to one molar equivalent of m-chloroperbenzoic acid can be used for this purpose, in a reaction-inert solvent such as methylene chloride or toluene, generally at a reduced temperature such as −10° to 10° C. When the sulfone is desired, a convenient oxidant is at least two molar equivalents of said m-chloroperbenzoic acid, otherwise in the same solvents and under the same mild conditions specified in the preceding sentence. However, a less expensive oxidant for formation of the sulfone is $H_2O_2$ in a reaction inert solvent such as acetic acid.

When a saturated compound of the formula (I) wherein the dotted line represents no bond is desired, an alternative synthetic route is to react thiazolidine-2,4-dione with a compound of the formula

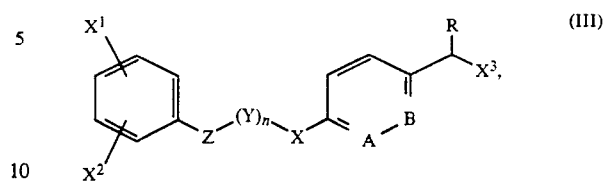

wherein A, B, R, X, $X^1$, $X^2$, Y, Z and n are as defined above, and $X^3$ is a nucleophilic leaving group such as chloride, bromide, iodide or mesylate. These reactants are generally used in substantially equimolar quantities, although 10–25% excess of readily available thiazolidine-2,4-dione is preferred in order to force the reaction to completion within a reasonable period of time. The reaction is carried out in the presence of reaction-inert solvent, such as tetrahydrofuran, with the thiazolidine-2,4-dione prereacted with two molar equivalents of a strong base such as butyl lithium in order to preform the dianion. Salt formation is generally carried out at reduced temperature (e.g. −50° to −80° C.), the reactants mixed at an intermediate temperature, and reaction carried to completion at an elevated temperature (e.g. the reflux temperature of the reaction mixture). It will be evident to those skilled in the art that this method will be preferred only when there are no other reactive groups (e.g., unprotected OH or ketonic carbonyl) present in the compound of the formula (III).

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, p-toluenesulfonate, acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

Thiazolidine-2,4-dione is commercially available. The aldehydes and ketones of formula (II) are prepared by a variety of conventional methods; for example, by mild oxidation of the corresponding primary or secondary alcohol with reagents such as manganese dioxide or chromic acid under conditions known to produce aldehydes from primary alcohols and ketones from secondary alcohols; reaction of the corresponding aralkyl bromides with n-butyl lithium followed by N,N-dimethylformamide at −80° to −70° C. reaction of a suitably 4-substituted benzaldehyde or acetophenone (or corresponding pyridine analog) with a suitably substituted benzene derivative so as to form the bridging group:

$$-(Z)_m-(Y)_n-X-.$$

For example:

$-CH_2NH(CH_3)+ClSO_2 \longrightarrow -CH_2N(CH_3)SO_2-$ $-CH_2CH_2SH+Br \longrightarrow -CH_2CH_2-S-$ $-SH+BrCH_2CH_2 \longrightarrow -S-CH_2CH_2-$ $-CH_2CH_2NH_2+ClCO \longrightarrow -CH_2CH_2NHCO-$ $-CHO+CH_3CO \longrightarrow -CH=CH-CO-$ $-CH=CH-CO \longrightarrow -CH_2CH_2-CO-$ $-CH=CH-CO \longrightarrow -CH_2CH_2CH_2-$ $-CH_2CH_2COOH \longrightarrow -CH_2CH_2-CO-$ The halides/mesylates of the formula (III) are also available by conventional methods, such as by the action of a suitable reagent (e.g., PBr₃, CH₃SO₂Cl or the corresponding alcohol), halogenation of a corresponding methyl derivative, and so forth.

It will be further evident to those skilled in the art that the synthesis of a compound of the formula (I) can be varied by coupling of a precursor ketone or aldehyde (or mesylate/halide) with thiazolidine-2,4-dione, with completion of the side chain as a later step, using one of the synthetic methods illustrated above for the preparation of ketones and aldehydes of the formula (II).

The present compounds of the formula (I) are readily adapted to clinical use as hypoglycemic agents. The activity required for this clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000×g at room temperature. The supernatant was analyzed for glucose, for example, by the ABA 200 Bichromatic Analyzer ™, using the A-gent ™ glucose UV reagent system* (hexokinase method) using 20, 60 and 100 mg/dl standards. Plasma glucose was then calculated by the equation, Plasma glucose (mg/dl) = Sample value × 5 × 1.67 = 8.35 × Sample value where 5 is the dilution factor and 1.67 is the plasma hematocrit adjustment (assuming the hematocrit is 40%).

™ A registered trademark of Abbott Laboratories, Diagnostics Division, 820 Mission Street, So. Pasadena, Calif. 91030.
*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) also effect the lowering of serum cholesterol levels in mammals.

Female mice (strain C57Br/cd J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at a dose in the range of 0.1 to 20 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Judged on the basis of LDL+VLDL cholesterol levels, total cholesterol levels or the ratio of LDL+VLDL/HDL, the compounds of the formula (I) show favorable results in lowering cholesterol levels.

The present compounds of the formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically-acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979. The abbreviations THF and DMF refer to tetrahydrofuran and dimethylformamide, respectively. Jones' Reagent refers to a solution of chromic anhydride in dilute sulfuric acid (Merck Index, 10th Edition, page ONR-49).

EXAMPLE 1

N-Benzyl-N-methyl-4-[(thiazolidine-2,4-dion-5-yl)methyl]benzenesulfonamide 2,4-Thiazolidinedione (11 mmol, 1.3 g) was dissolved in tetrahydrofuran (50 ml) and cooled to $-78°$ C. N-Butyllithium (22 mmol, 13.8 ml of 1.6M in hexane) was added over 15 minutes. The cooling bath was removed and the reaction mixture was stirred for 20 minutes. N-Benzyl-N-methyl-4-(bromomethyl)benzenesulfonamide (10 mmol, 3.5 g) dissolved in tetrahydrofuran (50 ml) was added over 20 minutes. The reaction mixture was heated to reflux for 15 hours, cooled and diluted with water (50 ml) and 6N HCl (10 ml). The mixture was extracted with ethyl acetate (75 ml) and the organic layer was dried ($Na_2SO_4$) and removed in vacuo. The residue was purified on silica gel using 1:1 hexane:ethyl acetate to afford 3.0 g of title product as a gum; MS 390 $(m^+)$, 269, 205.

Alternatively, 4-(thiazolidine-2,4-dion-5-yl)benzenesulfonyl chloride (9.6 mmol, 209 g) is dissolved in 100 ml of $CH_2Cl_2$ and cooled to $0°$ C. Benzylmethylamine (20.5 mmol, 2.5 g) dissolved in methylene chloride (5 ml) is added dropwise and the reaction stirred for 65 minutes. The solution is washed with 1N HCl ($2\times30$ ml), water ($2\times30$ ml), saturated NaCl ($2\times30$ ml), dried ($Na_2SO_4$) and solvent removed in vacuo. The residue is purified on silica gel as in the preceding paragraph to yield the same title product.

EXAMPLE 2

Sodium Salt of N-Benzyl-N-methyl-4-[(thiazolidine-2,4-dion-5yl)methyl]benzenesulfonamide The title product of the preceding Example (6.9 mmol, 2.7 g) was dissolved by warming in 75 ml of ethyl acetate. Sodium 2-ethylhexanoate (6.9 mmol, 1.1 g) in 10 ml ethyl acetate was added. Crystallization of product began within a few minutes. After standing overnight, present title product was recovered by filtration, 1.13 g; m.p. $279°$ C. (dec.), 1.03 g of which was recrystallized from 20 ml $H_2O$ to yield 0.44 g purified title product, m.p. $298°$ C.

Analysis calculated for $C_{18}H_{17}O_4N_2S_2Na$: C, 52.41; H, 4.16; N, 6.79%. Found: C, 52.09; H, 4.11; N, 6.68%.

EXAMPLE 3

N-Methyl-N-(2-phenylethyl)-4-[(thiazolidine-2,4-dion-5-yl)methyl]benzenesulfonamide By the method of Example 1, N-methyl-N-(2-phenylethyl)-4-(bromomethyl)benzenesulfonamide (10.6 mmol, 3.9 g) and thiazolidine-2,4-dione (11.7 mmol 1.4 g,), using 1:2 ethyl acetate:hexane as eluant, were converted to 3.3 g purified title product as a gum.

EXAMPLE 4

Sodium Salt of N-Methyl-N-(2-phenylethyl)-4-[(thiazolidine-2,4-dion-5-yl)methyl]benzenesulfonamide By the method of Example 2, the product of the preceding Example (3.7 mmol, 1.5 g) was converted, without recrystallization, to present title product, 0.74 g; m.p. $279°$ C. (dec.).

Analysis calculated for $C_{19}H_{19}O_4N_2S_2Na.0.33H_2O$: C, 52.77; H, 4.58; N, 6.48%. Found: C, 52.67; H, 4.52; N, 6.39%.

EXAMPLE 5

5-[4-(2-Phenylethylthio)phenylmethylene]thiazolidine-2,4-dione 4-(2-Phenylethylthio)benzaldehyde (12.4 mmol, 3.0 g), 2,4-thiazolidinedione (15.5 mmol, 1.81 g) and anhydrous sodium acetate (30.9 mmol, 2.54 g) were heated in an oil bath at $150°$ C. for 0.5 hour. The mixture was cooled and the resulting solid triturated with water (100 ml) and collected by filtration. The solid was recrystallized from methanol:ethyl acetate:acetone (1:1:2) to afford 500 mg of title product; m.p. $182°-183°$ C.

EXAMPLE 6

Sodium Salt of 5-[4-(2-Phenylethylthio)phenylmethylene]thiazolidine-2,4-dione

By the method of Example 2, the product of the preceding Example (0.15 mmol, 50 mg) was converted to present title product, 40 mg; m.p. $236°$ C. (dec.).

Analysis calculated for $C_{18}H_{14}O_2NS_2Na$: C, 59.48; H, 3.88; N, 3.85%.

Found: C, 59.95; H, 4.16; N, 3.79%.

EXAMPLE 7

5-[4-(2-Phenylethylthio)benzyl]thiazolidine-2,4-dione

Title product of Example 5 (4.1 mmol, 1.4 g) and zinc dust (40 mmol, 2.6 g) were heated to reflux in acetic acid (50 ml) for 15 minutes. The reaction mixture was filtered and the solvent was removed in vauco. The residue was purified on silica gel using hexane:ethyl acetate (2:1) plus 5% acetic acid as eluant to afford 230 mg of present title product; m.p. 58°–65° C.

Analysis calculated for $C_{18}H_{17}NO_2S_2$: C, 62.97; H, 4.99; N, 4.08%. Found: C, 62.94; H, 5.13; N, 3.91%.

The corresponding sodium salt was prepared according to the method of Example 2; 215 mg from 230 mg; m.p. greater than 250° C.

EXAMPLE 8

5-[4-(2-Phenylethylsulfinyl)benzyl]thiazolidine-2,4-dione

Title product of the preceding Example (5.8 mmol, 2.0 g) was dissolved in methanol (125 ml) and added to sodium periodate (17.4 mmol, 3.7 g) dissolved in water (40 ml) at room temperature. The reaction mixture was stirred for 1 hour and then concentrated to 50 ml. Water (150 ml) was added and the solution was extracted with ethyl acetate (2×125 ml). The organic layers were washed with water (50 ml), saturated NaCl (50 ml), dried ($Na_2SO_4$) and solvent removed in vacuo. The residue was purified on silica gel using hexane:ethyl acetate (1:1) followed by ethyl acetate as eluant to afford 1.0 g of product which was crystallized from ethyl acetate:carbon tetrachloride to yield 0.74 g of purified title product; m.p. 130°–132° C.

Analysis calculated for $C_{18}H_{17}O_3NS_2$: C, 60.14; H, 4.77; N, 3.90%. Found: C, 60.05; H, 4.77; N, 3.85%.

EXAMPLE 9

Sodium Salt of 5-[4-(2-Phenylethylsulfinyl)benzyl]thiazolidine-2,4-dione

By the method of Example 2, the title product of the preceding Example (3.6 mmol, 1.3 g) was converted, without recrystallization, to 1.14 g of present title product; m.p. 205° C. (dec.).

Analysis calculated for $C_{18}H_{16}O_3NS_2Na$: C, 56.67; H, 4.23; N, 3.67%. Found: C, 56.40; H, 4.25; N, 3.61%.

EXAMPLE 10

Sodium Salt of 5-[4-(2-Phenylethylsulfonyl)phenylmethylene]thiazolidine-2,4-dione m-Chloroperbenzoic acid (11.6 mmol, 2.5 g, 80%) was suspended in methylene chloride (75 ml) and cooled to 0° C. Title product of Example 5 (5.27 mmol, 1.8 g) was added and the reaction mixture stirred for 1 hour. Aqueous sodium sulfite was added and the solid was collected by filtration. Recrystallization from ethyl acetate afforded 0.44 g of the free acid form of present title product; m.p. 225°–226° C. The free acid (0.13 mmol, 50 mg) was converted to 38 mg of the title sodium salt according to the method of Example 2, without recrystallization; m.p. 265° C. (dec.).

Analysis calculated for $C_{18}H_{14}O_4N_2S_2Na$: C, 54.67; H, 3.57; N, 3.54%. Found: C, 54.69; H, 3.92; N, 3.46%.

EXAMPLE 11

5-[4-(2-Phenylethylsulfonyl)benzyl]thiazolidine-2,4-dione

Free acid form of the product of the preceding Example (1.34 mmol, 500 mg) was hydrogenated in a Paar shaker using 10% Pd/C sulfur resistant catalyst (300 mg) at 50 psig for 18 hours at room temperature in THF (50 ml). The catalyst was removed by filtration, the solvent removed in vacuo, and the residue recrystallized from ethyl acetate to afford present title product, 400 mg; m.p. 201°–203° C.

Analysis calculated for $C_{18}H_{17}NO_4S_2$: C, 57.58; H, 4.57; N, 3.73%. Found: C, 57.82; H, 4.64; N, 3.71%.

EXAMPLE 12

Sodium Salt of 5-[4-(2-Phenylethylsulfonyl)benzyl]thiazolidine-2,4-dione

By the method of Example 2, without recrystallization, the product of the preceding Example (1.33 mmol, 500 mg) was converted to 380 mg of present title product; m.p. 288° C. (dec.).

Analysis calculated for $C_{18}H_{16}O_4NS_2Na$: C, 54.39; H, 4.06; N, 3.52%. Found: C, 53.53; H, 4.19; N, 3.36%.

EXAMPLE 13

5-[1-(4-(2-Phenylethylthio)phenyl)ethylidene]thiazolidine-2,4-dione 4-(2-Phenylethylthio)acetophenone (30 mmol, 7.7 g), 2,4-thiazolidinedione (30 mmol, 3.5 g) and sodium acetate (60 mmol, 4.9 g) were fused in an oil bath at 190° C. for 0.5 hour. The solid was cooled and dissolved in water (50 ml) and ethyl acetate (50 ml). The layers were separated and the ethyl acetate washed with water (2×50 ml), dried ($Na_2SO_4$) and stripped in vacuo. The residue was crystallized from ether to afford 1.7 g of title product; m.p. 183°–187° C.

Analysis calculated for $C_{19}H_{17}O_2NS_2$: C, 64.19; H, 4.82; N, 3.94%. Found: C, 64.73; H, 4.81; N, 3.36%.

The corresponding sodium salt was prepared according to the method of Example 2.

EXAMPLE 14

5-[1-(4-(2-Phenylethylthio)phenyl)ethyl]thiazolidine-2,4-dione

By the method of Example 7, the title product of the previous Example was converted to present chromatographically purified title product as an oil.

Analysis calculated for $C_{19}H_{19}O_2NS_2$: C, 63,86; H, 5.36; N, 3.92%. Found: C, 63.67; H, 5,42; N, 3.94%.

The corresponding sodium salt was prepared according to the method of Example 2, without recrystallization; m.p. 260°–265° C.

EXAMPLE 15

5-[1-(4-(2-Phenylethylsulfonyl)phenyl)ethyl]thiazolidine-2,4-dione

Title product of the preceding Example (1 mmol, 360 mg) was dissolved in acetic acid (20 ml) at room temperature. 30% Hydrogen peroxide (5 ml) was added and the mixture stirred for 18 hours. The solution was diluted with water (75 ml) and stirred for 2 hours to afford a gummy precipitate. The liquid was decanted and the residue triturated with water (10 ml) and hexane (10 ml) to afford 200 mg of present title product as a white solid; m.p. 135°–145° C.

Analysis calculated for $C_{19}H_{19}O_4NS_2$: C, 58.61; H, 4.92; N, 3.60%. Found: C, 58.86; H, 4.95; N, 3.55%.

The corresponding sodium salt was prepared according to the method of Example 2.

EXAMPLE 16

5-[1-(4-(2-Phenylethylsulfonyl)phenyl)ethylidene[-thiazolidine-2,4-dione

Title product of Example 13 (1.41 mmol, 500 mg) was added to a solution of m-chloroperbenzoic acid (3.10 mml, 535 mg) slurried in methylene chloride (15 ml) at 0° C. The reaction mixture was stirred for 1 hour at room temperature. The mixture was diluted with $CHCl_3$ (60 ml), washed with 10% $Na_2SO_3$ (20 ml), saturated $NaHCO_3$ (2×20 ml) and saturated NaCl (20 ml), dried ($Na_2SO_4$), and solvent removed in vacuo. The crude solid was recrystallized from acetic acid to afford present title product as yellow crystals; m.p. 201°–202° C.

Analysis calculated for $C_{19}H_{17}O_4NS_2$: C, 58.89; H, 4.42; N, 3.62%. Found: C, 58.65; H, 4.63; N, 3.46%.

The corresponding sodium salt was prepared, without recrystallization, according to the method of Example 2; m.p. 269° C. (dec.).

EXAMPLE 17

5-[4-(2-(4-Chlorophenyl)ethylthio)phenylmethylene]-thiazolidine-2,4-dione

4-[2-(4-Chlorophenyl)ethylthio]benzaldehyde and thiazolidine-2,4-dione were coupled according to the method of Example 5 to form present title product in similar yield; m.p. 215°–225° C.

Analysis calculated for $C_{18}H_{14}ClNO_2S_2$: C, 57.51; H, 3.76; N, 3.73%. Found: C, 57.27; H, 3.77; N, 3.59%.

EXAMPLE 18

Sodium Salt of 5-[4-(2-(4-Chlorophenyl)ethylthio)phenylmethylene]-thiazolidine-2,4-dione By the method of Example 2, without recrystallization, the title product of the preceding Example was converted to present title product in similar yield; m.p. greater than 240° C.

Analysis calculated for $C_{18}H_{13}ClNO_2S_2Na$: C, 54.33; H, 3.29; N, 3.52%. Found: C, 54.34; H, 3.45; N, 3.31%.

EXAMPLE 19

Sodium Salt of 5-[4-(2-(4-Chlorophenyl)ethylthio)benzl]thiazolidine-2,4-dione

By the method of Example 7, the title product of Example 17 (9.84 mmol, 3.7 g) was reduced to present title product, chromatographed on silica gel using 4:1 hexane:ethyl acetate as eluant, initially isolating the free acid form of title product as an oil (1.3 g) which solidified on pumping under vacuum; m.p. 100° C.

The free acid was converted to title sodium salt by dissolving the free acid (2.14 mmol, 0.875 g) in 10 ml $CH_3OH$ and 10 ml of ethyl acetate with warming, adding 2.14 ml of 1M $NaOC_2H_5$ in ethanol (2.14 mmol), stirring 30 minutes, stripping away solvent and triturating the residue with ether to yield 0.8 g of title product; m.p. greater than 250° C.

Analysis calculated for $C18H15ClNO_2S_2Ha$: C, 54.06; H, 3.78; N, 3.50%. Found: C, 53.79; H, 3.76; N, 3.39%.

EXAMPLE 20

5-[4-(2-(4-Chlorophenyl)ethylsulfonyl)phenylmethylene]thiazolidine-2,4-dione

By the method of Example 10, the title product of Example 17 (23.2 mmol, 5 g) was oxidized to 2.4 g of present title product following recrystallization from ethyl acetate; m.p. 242°–243° C.

Free acid (1.3 g) was converted to 1.36 g of the corresponding sodium salt by the method used in the preceding Example; m.p. greater than 250° C.

EXAMPLE 21

Sodium Salt of 5-[4-(2-(4-Chlorophenyl)ethylsulfonyl)benzyl]thiazolidine-2,4-dione By the method of Example 11, the title product of the preceding Example (1.7 g) was hydrogenated to produce present title product, purified by chromatography on silica gel using gradient elution with 4:1, 3:1 and finally 2:1 hexane:ethyl acetate to yield 0.93 g of the purified free acid form title product as a white solid; m.p. 168°–171° C.

The latter (0.9 g) was converted to 0.85 g of the sodium salt according to the method of Example 19; m.p. greater than 250° C.

Analysis calculated for $C_{18}H_{15}ClNO_4S_2Na$: C, 54.06; H, 3.78; N, 3.50%. Found: C, 53.79; H, 3.76; N, 3.39%.

EXAMPLE 22

5-[4-(Benzylthio)phenylmethylene]thiazolidine-2,4-dione 4-(Benzylthio)benzaldehyde (20.8 g) was fused with thiazolidine-2,4-dione according to the method of Example 5 to afford 15 g of present title product; m.p. 237°–238° C.

EXAMPLE 23

Sodium Salt of 5-[4-(Benzylthio)phenylmethylene]thiazolidine-2,4-dione

By the method of Example 2, without recrystallization, the title product of the preceding Example was converted to present title product in similar yield; m.p. greater than 250° C.

EXAMPLE 24

5-[4-(Benzylthio)benzyl]thiazolidine-2,4-dione

By the method of Example 7, the title product of Example 22 (1.31 g) gave, after recrystallization from ether:hexane, 0.35 g of present title product; m.p. 102°–103° C.

Analysis calculated for $C_{17}H_{15}NO_2S_2$: C, 61.97; H, 4.59; N, 4.25%. Found: C, 62.24; H, 4.51; N, 4.16%.

The corresponding sodium salt was prepared according to Example 2; m.p. greater than 250° C.

EXAMPLE 25

Sodium Salt of 5-[4-(Benzylsulfonyl) benzyl]thiazolidine-2,4-dione

By the method of Example 10, the title product of the preceding Example (2.0 g) was converted, after recrystallization from ethyl acetate, to 1.14 g of the free acid form of present title product; m.p. 175° C.

The sodium salt was prepared according to Example 19 in similar yield; m.p. greater than 250° C.

Analysis calculated for $C_{17}H_{14}NO_4S_2Na$: C, 53.25; H, 3.68; N, 3.65%. Found: C, 55.36; H, 3.74; N, 3.58%.

EXAMPLE 26

5-[4-(3-Phenylpropylthio)phenylmethylene]thiazolidine-2,4-dione

By the method of Example 5, 4-(3-phenylpropylthio)benzaldehyde (7.0 mmol, 1.8 g) gave 1.8 g of title product, recrystallized from acetic acid; m.p. 172°-173° C.

Analysis calculated for $C_{19}H_{17}O_2NS_2$: C, 64.19; H, 4.82; N, 3.94%. Found: C, 64.18; H, 4.75; N, 3.76%.

EXAMPLE 27

Sodium Salt of 5-[4-(3-Phenylpropylthio)phenylmethylene]thiazolidine-2,4-dione

By the method of Example 2, without recrystallization, title product of the preceding Example (1.0 g) was converted to 0.98 g of present title product; m.p. 240°-275° C. (dec.).

EXAMPLE 28

5-[4-(3-Phenylpropylthio)benzyl]thiazolidine-2,4-dione

By the method of Example 7, the title product of Example 26 (1.8 g) was reduced to 0.49 g of present title product, recrystallized from 1:1 hexane:isopropyl ether; m.p. 88°-89° C.

Analysis calculated for $C_{19}H_{19}O_2NS_2$: C, 63.83; H, 5.36; N, 3.92%. Found: C, 64.27; H, 5.43; N, 3.87%.

EXAMPLE 29

Sodium Salt of 5-[4-(3-Phenylpropylthio)benzyl]thiazolidine-2,4-dione

By the method of Example 2, without recrystallization, the title product of the preceding Example (1.5 g) was converted to 1.09 g of present title product; m.p. 286° C. (dec.).

EXAMPLE 30

Sodium Salt of 5-[4-(3-Phenylpropylsulfinyl)benzyl]thiazolidine-2,4-dione

By the method of Example 8, the title product of Example 28 (3.9 mmol, 1.4 g) was converted to 1.2 g of chromatographed free acid form title product as a gum; tlc Rf 0.3 (ethyl acetate). The latter was converted to 1.29 g of sodium salt according to the method of Example 2 (without recrystallization); m.p. 210° C. (dec.).

Analysis calculated for $C_{19}H_{18}O_3NS_2Na$: C, 57.70; H, 4.59; N, 3.54%. Found: C, 57.31; H, 4.57; N, 3.42%.

EXAMPLE 31

5-[4-(3-Phenylpropylsulfonyl)phenylmethylene]thiazolidine-2,4-dione

By the method of Example 10, the title product of Example 26 (4.0 mmol, 1.42 g) was converted to 1.1 g of present title product recrystallized from acetic acid; m.p. 224°-225° C.

Analysis calculated for $C_{19}H_{17}O_4NS_2$: C, 58.89; H, 4.42; N, 3.62%. Found: C, 59.16; H, 4.24; N, 3.55%.

EXAMPLE 32

Sodium Salt of 5-[4-(3-Phenylpropylsulfonyl)phenylmethylene]thiazolidine-2,4-dione By the method of Example 2, without recrystallization, title product of the preceding Example (1.22 g) was converted to 1.19 g of present title product; m.p. 255° C. (dec.).

EXAMPLE 33

5-[4-(3-Phenylpropylsulfonylbenzyl]thiazolidine-2,4-dione

By the method of Example 11, the title product of Example 31 (1.0 g) was converted to 0.85 g of present title product purified by silica gel chromatography using 1:1 hexane:ethyl acetate as eluant, initially isolated as an oil which crystallized on standing; m.p. 126°-127° C.

Analysis calculated for $C_{19}H_{19}O_4NS_2$: C, 58.59; H, 4.92; N, 3.60%. Found: C, 58.86; H, 5.00; N, 3.54%.

EXAMPLE 34

Sodium Salt of 5-[4-(3-Phenylpropylsulfonyl)benzyl]thiazolidine-2,4-dione

By the method of Example 2, without recrystallization, the title product of the preceding Example (1.54 mmol, 0.60 g) was converted to 0.52 g of present title product; m.p. 288° C. (dec.).

Analysis calculated for $C_{19}H_{18}O_4NS_2Na$: C, 55.46; H, 4.41; N, 3.40%. Found: C, 55.53; H, 4.38; N, 3.13%.

EXAMPLE 35

5-[4-(2-(Phenylthio)ethyl)phenylmethylene]thiazolidine-2,4-dione

By the method of Example 5, 4-[2-(phenylthio)ethyl]benzaldehyde (26 mmol, 6.3 g) was converted to 6.0 g of present title product following recrystallization from acetic acid; m.p. 159°-161° C.

Analysis calculated for $C_{18}H_{15}O_2NS_2$: C, 63.31; H, 4.43; N, 4.10%. Found: C, 63.25; H, 4.37; N, 4.02%.

EXAMPLE 36

Sodium Salt of 5-[4-(2-(Phenylthio)ethyl)phenylmethylene]thiazolidine-2,4-dione

By the method of Example 2, without recrystallization, the title product of the preceding Example (1.54 mmol, 0.525 g) was converted to 0.50 g of present title product; m.p. 270° C. (dec.).

Analysis calculated for $C_{18}H_{14}O_2NS_2Na$: C, 59.48; H, 3.88; N, 3.85%. Found: C, 59.24; H, 3.85; N, 3.72%.

EXAMPLE 37

Sodium Salt of 5-[4-(2-(Phenylthio)ethyl)benzyl]thiazolidine-2,4-dione

By the method of Example 7, title product of Example 35 (2.9 mmol, 1.0 g) was converted to 0.26 g of the purified free acid form of present title product, isolated from the chromatography as a gum.

Analysis calculated for $C_{18}H_{17}O_2NS_2$: C, 62.94; H, 4.99; N, 4.08%. Found: C, 62.73; H, 5.01; N, 3.95%.

The free acid (1.76 g) was converted to 1.2 g of the corresponding sodium salt by the method of Example 2 (without recrystallization); m.p. 290° C. (dec.).

Analysis calculated for $C_{18}H_{16}O_2NS_2Ha$: C, 59.15; H, 4.41; N, 3.83%. Found: C, 58.77; H, 4.37; N, 3.78%.

EXAMPLE 38

Sodium Salt of 5-[4-(2-(Phenylsulfonyl)ethyl)benzyl]thiazolidine-2,4-dione

By the method of Example 10, the free acid form of the title product of the preceding Example (4.1 mmol, 1.4 g) was converted to 0.70 g of the free acid form of present title product, isolated as a gum from chromatography on silica gel using 1:1 hexane:ethyl acetate as eluant.

Analysis calculated for $C_{18}H_{17}O_4NS_2$: C, 57.58; H, 4.56; N, 3.73%. Found: C, 57.96; H, 4.70; N, 3.49%.

The sodium salt was formed according to the method of Example 2; m.p. 285° C. (dec.).

Analysis calculated for $C_{18}H_{16}O_4NS_2Na$: C, 54.39; H, 4.06; N, 3.52%. Found: C, 54.11; H, 4.20; N, 3.40%.

EXAMPLE 39

(E)-5-[4-(3-Phenyl-2-propenoyl)benzyl]thiazolidine-2,4-dione

To a slurry of 5-(4-acetylbenzyl)thiazolidine-2,4-dione (4.0 mmol, 1.0 g), and benzaldehyde (4.0 mmol, 0.41 ml) in ethanol (10 ml) was added sodium methoxide (4.8 mmol, 260 mg). The solution was heated to reflux for 1.5 hours, then more benzaldehyde was added and the mixture was heated another 1.5 hours, then cooled, diluted with water (60 ml), acidified with 2N HCl and extracted with ethyl acetate (2×50 ml). The combined extracts were washed with water (50 ml), dried over sodium sulfate and concentrated in vacuo. The residue was recrystallized from isopropanol to give title product as a pale yellow solid (0.33 g, 24%); m.p. 147°-149° C.

Analysis calculated for $C_{19}H_{15}NO_3S$: C, 67.63; H, 4.48; N, 4.15%. Found: C, 67.40; H, 4.57; N, 4.00%.

EXAMPLES 40-52

(E)-5-[4-(3-(Substituted-phenyl)-2-propenopyl)benzyl]thiazolidine-2,4-dione

Substituting a molar equivalent of the appropriately substituted benzaldehyde for benzaldehyde in the process of Example 39 gave the following additional compounds:

| No. | Phenyl Substit.[f] | Rx[a] or Ch[a] Solvent[f] | Yield (%) | HRMS[i] Calcd. (Found) | m.p. (°C.) |
|---|---|---|---|---|---|
| 40 | 2-OCH$_3$ | None | 81 | 367.0915 (367.0878) | 88-9 (dec.) |
| 41 | 2-Cl | Rx HOAc | 52 | — | 193-6 |
| 42[b] | 2-CF$_3$ | Ch CHCl$_3$:CH$_3$OH 20:1 | 22 | 405.0684 (405.0646) | 251-4[c] |
| 43[d] | 2-CH$_2$Ph | None | 32 | — | 235-8[c] |
| 44[d] | 2-OCH$_2$OMe | Ch hexane:EtOAc 1:1 | 36 | — | 285 (dec.) |
| 45[d] | 2-CH$_3$ | None | 5 | — | 250[c] (dec.) |
| 46 | 4-OCH$_2$Ph | Rx Me$_2$CHOH | 73 | 443.1194 (443.1192) | 240 (dec.) |
| 47[d] | 4-Br | None | 45[e] | — | above 300° C. |
| 48[d] | 4-Ph | None | 60 | 413.1099 (413.1086) | above 300° C. |
| 49 | 4-NO$_2$ | None | 68 | 382.0578 (382.0623) | 245[c] (dec.) |
| 50 | 3-Cl | None | 41 | — | 264-6[c] |
| 51[b] | 3-NO$_2$ | Ch hexane:EtOAc 1:1 | 52 | — | 265[g] |
| 52[h] | 4-OCH$_2$OMe | Ch 3% CH$_3$OH in CHCl$_3$ | 36 | — | 285[c] |

[a]Rx = recrystallization; Ch = chromatography.
[b]Dimethylsulfoxide used in place of ethanol.
[c]As the sodium salt, obtained by combining 360 mg of free acid with a molar equivalent of NaOCH$_3$ in 10 ml CH$_3$OH, and evaporation.
[d]KOC(CH$_3$)$_3$ used in place of NaOCH$_3$.
[e]Initially isolated as the potassium salt in 82% yield.
[f]Ph = phenyl; Me = methyl; HOAc = acetic acid; EtOAc = ethyl acetate.
[g]As the sodium salt, 395 mg obtained according to the method of Example 2 from 500 mg of free acid; Analysis calculated for $C_{19}H_{13}N_2O_5SNa$: C, 56.43; H, 3.24; N, 6.93%. Found: C, 56.27; H, 3.02; N, 6.27%.
[h]NaOH in place of NaOCH$_3$ and 1:1 H$_2$O:CH$_3$OH in place of ethanol.
[i]HRMS = High Resolution Mass Spectroscopy.

EXAMPLE 53

(E)-5-[4-(3-(2-Hydroxyphenyl)-2-propenoyl)benzyl]thiazolidine-2,4-dione

The product of Example 44 (310 mg, 0.78 mmol) was dissolved in THF (5 ml) and 3M sulfuric acid (3 ml). After 2 hours the solution was diluted with water (75 ml) and extracted with ethyl acetate (2×75 ml). The combined extracts were washed with water (2×50 ml), brine (50 ml), dried over sodium sulfate and concentrated in vacuo, leaving present title product as a yellow gummy foam (247 mg, 90%).

The sodium salt was prepared as described for Example 42 and obtained as an orange solid; m.p. 108° C. (dec.).

Analysis calculated for $C_{19}H_{14}NO_3SNa \cdot \frac{1}{2}H_2O$: C, 59.36; H, 3.93; N, 3.64%. Found: C, 59.07; H, 4.12; N, 3.43%.

By the same method, the product of Example 52 is converted to (E)-5-[4-(3-(4-hydroxyphenyl)-2-propenoyl)benzyl]thiazolidine-2,4-dione.

EXAMPLE 54

(E)-5-[4-(3-(2-Methanesulfonyloxyphenyl)-2-propenoyl)benzyl]thiazolidine-2,4-dione To a solution of the title product of the preceding Example (246 mg, 0.70 mol) in dichloromethane (10 ml) was added triethylamine (0.12 ml, 0.84 mmol), followed by methanesulfonyl chloride (0.070 ml, 0.84 mmol). The solution was stirred for 3 hours at room temperature, then diluted with dichloromethane (40 ml) and washed with water (25 ml), saturated aqueous sodium bicarbonate (2×25 ml), water (25 ml) and brine (25 ml), dried over sodium sulfate and concentrated in vacuo. After flash-chromatography (hexane:ethyl acetate 1:2) present title product was obtained as a yellow solid (82 mg, 27%).

HRMS ($C_{20}H_{17}NO_6S_2$). Calc.: 352.0643. Found 352.0667.

The sodium salt was prepared as described for Example 42 and obtained as a yellow solid; m.p. 198°–200° C.

EXAMPLE 55

(E)-5-[4-(3-(4-Methoxyphenyl)-2-propenoyl)benzyl]-thiazolidine-2,4-dione

Hydrogen chloride was bubbled into an ice-cooled solution of 5-(4-acetylbenzyl)thiazolidine-2,4-dione (1.0 g, 4.0 mmol) and p-anisaldehyde (0.55 g, 4.0 mol) in ethanol (15 ml) for 1 hour. The solution was stirred overnight at room temperature, then diluted with water and the yellow precipitate of present title product collected and dried (1.37 g, 93%); m.p. 177°–180° C.

HRMS ($C_{20}H_{16}NO_4S$ M-H+). Calc.: 366.0800. Found: 366.0939.

The sodium salt was prepared as described in Example 42; m.p. 275°–280° C.

EXAMPLE 56

(E)-5-[4-(3-(4-Acetylaminophenyl)-2-propenoyl)benzyl]thiazolidine-2,4-dione

By the method of the preceding Example, 4-acetylaminobenzaldehyde (0.65 g, 4.0 mmol) was converted to present title product (1.36 g, 86%).

HRMS ($C_{21}H_{18}N_2O_4S$). Calc.: 394.0988. Found: 394.1009.

The sodium salt was prepared as described in Example 42; m.p. 250° C. (dec.).

EXAMPLE 57

5-[4-(3-Phenylpropionyl)benzyl]thiazolidine-2,4-dione

To an ice-cooled solution of the title product of Example 39 (2.0 g, 5.9 mmol) in trifluoroacetic acid (20 ml) was added triethylsilane (0.95 ml, 5.9 mmol). The mixture was stirred for 25 minutes at 0° C., then diluted with water (50 ml) and extracted with ether (2×40 ml). The combined extracts were washed with water (2×40 ml) and 5% sodium bicarbonate (2×40 ml), dried over sodium sulfate and concentrated in vacuo. The residue was triturated with hexane to give present title product as a pale yellow solid (1.65 g, 82%); m.p. 119°–121° C.

The sodium salt was prepared as described in Example 42; m.p. greater than 230° C.

EXAMPLES 58–61

5-[4-(3-Substituted-phenyl)propionyl)benzylthiazolidine-2,4-dione

Substituting the appropriate 5-[4-(3-(substituted-phenyl)-2-propenoyl)benzyl]thiazolidine-2,4-dione for the title product of Example 39 in the preceding Example gave the following additional compounds:

| No. | Phenyl Substit. | Chromatog. Solvent | Yield (%) | HRMS Calcd. (Found) | m.p. (°C.) |
|---|---|---|---|---|---|
| 58 | 2-OCH$_3$ | None | 72 | — | 269 (dec.)[a,b] |
| 59 | 4-CH$_2$Ph | 5% CH$_3$OH in CHCl$_3$ | 77 | 445.1367 (445.1347) | 97–101 |
| 60 | 4-Ph | 5% CH$_3$OH in CHCl$_3$ | 55 | 415.1230 (415.1242) | 270[a] |
| 61 | 4-OCH$_3$ | hexane:ETOAc 2:3 | 36 | — | 272–4[a] |

[a]As the sodium salt
[b]Analysis calculated for $C_{20}H_{18}NO_4SNa$: C, 61.37; H, 4.63; N, 3.58%. Found: C, 61.15; H, 4.63; N, 3.53%.

EXAMPLE 62

5-[4-(3-(3-Methoxyphenylpropionyl)benzyl]thiazolidine-2,4-dione

3-[4-[3-(3-Methoxyphenyl)propionyl]phenyl]-2-bromopropionic acid (0.73 mg, 1.9 mmol) and thiourea (0.28 g, 3.7 mmol) were dissolved in sulfolane (1 ml) and heated to 105°–110° C. for 5 hours. 2N HCl (1 ml) was then added and the solution was heated to 105°–110° C. overnight. The mixture was cooled, diluted with water (30 ml) and extracted with ethyl acetate (2×30 ml). The combined extracts were washed with water (4×30 ml) and brine (40 ml), dried over sodium sulfate and concentrated in vacuo. The product was purified by flash-chromatography (hexane:ethyl acetate, 1:1), to give present title product as a gummy solid.

The sodium salt was prepared as described in Example 2; m.p. 274° C. (dec.).

EXAMPLE 63

5-[4-(1-Hydroxy-3-phenylpropyl)benzyl]thiazolidine-2,4-dione

To an ice-cooled solution of title product of Example 57 (1.65 g, 4.9 mmol) in methanol (35 ml) was added sodium borohydride (185 mg, 4.9 mmol). The solution was stirred for 2 hours at room temperature, then quenched with 1N HCl, diluted with water (100 ml) and extracted with ethyl acetate (3×50 ml). The combined extracts were washed with water (50 ml) and brine (50 ml), dried over sodium sulfate and concentrated in vacuo, leaving present title product as an oil (1.61 g, 97%).

The sodium salt was prepared in 77% yield as described in Example 42; m.p. 249°–254° C.

EXAMPLE 64

5-[4-(3-Phenylpropyl)benzyl]thiazolidine-2,4-dione

A solution of the title product of Example 39 (2.0 g, 5.9 mmol) in trifluoroacetic acid (20 ml), cooled to 0° C., was treated with triethylsilane (2.8 ml, 18 mmol). After 25 minutes at 0° C., the solution was diluted with water (60 ml) and extracted with ether (2×50 ml). The combined extracts were washed with water (2×50 ml)

and brine (50 ml), dried over sodium sulfate and concentrated in vacuo, leaving a brown oil. Present title product was isolated by flash-chromatography (hexane:ethyl acetate, 5:1) as an oil (1.11 g, 58%).

The sodium salt was prepared as described in Example 42; m.p. 286° C.

EXAMPLE 65

5-[4-(3-Phenyl-2,3-epoxypropionyl)benzyl]thiazolidine-2,4-dione

To a solution of title product of Example 39 (0.5 g, 1.5 mmol) in methanol (4 ml), cooled to 0° C., was added 30% $H_2O_2$ (0.5 ml, 4.8 mmol), followed by 2N NaOH (1.6 ml, 3.2 mmol). After 30 minutes at 0° C. the solution was acidified with 2N HCl, diluted with water (15 ml) and extracted with ethyl acetate (2×15 ml). The combined extracts were washed with brine (15 ml), dried over magnesium sulfate and concentrated in vacuo, leaving present title product as an oil (420 mg, 80%). HRMS ($C_{19}H_{15}NO_4S$). Calc.: 353.0721. Found: 353.0755.

The sodium salt was prepared as described in Example 42; m.p. 207°–209° C.

EXAMPLE 66

5-[4-(4-Phenylbutyryl)phenylmethylene]thiazolidine-2,4-dione

An intimate mixture of the title product of Preparation 20 (2.35 g, 9.3 mmol), sodium acetate (2.29 g, 27.9 mmol) and 2,4-thiazolidinedione (1.64 g, 1.4 mmol) was heated to 150° C. for 30 minutes. After cooling, the contents of the flask were cooled, pulverized and washed with water (50 ml) and then 5% methanol in ether (40 ml). The product was dried to afford 2.92 g (93%) of present title product as a yellow solid; m.p. greater than 280° C.

EXAMPLE 67

5-[(2-(3-Phenylpropionyl)-5-pyridyl)methylene]-thiazolidine-2,4-dione

By the method of the preceding Example, title product of Preparation 21 was converted to present title product in 96% yield; m.p. greater than 250° C.

EXAMPLE 68

5-[(5-(3-Phenylpropionyl)-2-pyridyl)methylene]-thiazolidine-2,4-dione

By the method of Example 66, title product of Preparation 22 was converted to present title product in quantitative yield; m.p. greater than 250° C.

EXAMPLE 69

Sodium Salt of 5-[4-(4-Phenyl-1-hydroxybutyl)benzyl]thiazolidine-2,4-dione

To the title product of Example 66 (2.80 g, 8.3 mmol) in methanol (100 ml) was added 3% sodium amalgam (100 g) and the reaction mixture was stirred for 4 hours at ambient temperature. The organic solution was then decanted, concentrated, diluted with water (100 ml) and acidified to pH 2 with 2N HCl. The aqueous was extracted with $CH_2Cl_2$ (3×50 ml), dried and concentrated to give 796 mg of a colorless oil. Purification via radial chromatography (2% $CH_3OH$ in $CH_2Cl_2$) gave the free acid form of present title product (178 mg, 6%) isolated as an oil.

To a solution of the latter (85 mg, 0.25 mmol) in a small amount of methanol was added sodium methoxide (15 mg, 0.28 mmol). The reaction was concentrated to dryness and triturated with 1:10 $CH_3OH$:ether (5 ml) and then filtered to afford 27 mg (29%) of present title product; m.p. 244°–246° C.

EXAMPLE 70

5-[(2-(3-Phenyl-1-hydroxypropyl)-5-pyridyl)methyl]-thiazolidine-2,4-dione

To a solution of the title product of Example 67 (260 mg, 0.77 mmol) in methanol (10 ml) was added 3% sodium amalgam (4 g) and the reaction was stirred for 4 hours. The methanol was decanted, evaporated and the resultant solid diluted with water (10 ml). The aqueous solution was adjusted to pH 2 with 1N HCl and extracted with $CH_2Cl_2$ (3×10 ml) which was discarded. After neutralization of the aqueous layer to pH 7 with $NaHCO_3$, it was then re-extracted with $CH_2Cl_2$ (3×10 ml). These combined organic layers were dried ($MgSO_4$), filtered and concentrated to afford the desired product (94 mg, 36%) isolated as a foam.

EXAMPLE 71

5-[(5-(3-Phenyl-1-hydroxypropyl)-2-pyridyl)methyl]-thiazolidine-2,4-dione

By the method of Example 69, the title product of Example 68 was converted to present chromatographed title product as an oil in 34% yield.

EXAMPLE 72

Sodium Salt of 5-[(5-(3-Phenyl-1-hydroxypropyl)-2-pyridyl)methyl]-thiazolidine-2,4-dione To a solution of title product of the preceding Example (70 mg, 0.20 mmol) in ethyl acetate (1 ml) was added sodium 2-ethylhexanoate (32 mg, 0.19 mmol) and ether (1 ml). After stirring for 1 hour, the white solid was collected via vacuum filtration and dried to give the expected product (43 mg, 60%) isolated as a white solid; m.p. 251° C. (dec.).

EXAMPLE 73

5-[4-(4-Phenylbutyryl)benzyl]thiazolidine-2,4-dione

To a solution of the title product of Example 66 (145 mg, 0.408 mmol) in acetone (10 ml) at 0° C. was added in a dropwise fashion Jones' Reagent (2.67M, 0.39 ml, 1.0 mmol). After stirring for 2 hours at room temperature, the reaction was quenched by the addition of isopropanol (1 ml) followed by water (20 ml), and stirred 10 minutes. The blue solution was decanted and extracted with EtOAc (2×20 ml). The combined organic layers were washed with water (20 ml), brine (20 ml), dried ($MgSO_4$), filtered and concentrated to afford the present title product (129 mg, 90%); m.p. 120°–122° C.

EXAMPLE 74

5-[4-(3-Phenyl-2-propenoyl)phenylmethylene]thiazolidine-2,4-dione

A solution of 5-(4-acetylphenylmethylene)thiazolidine-2,4-dione (1.0 g, 4.0 mmol) and benzaldehyde (0.62 ml, 6.1 mmol) in 1N NaOH (14 ml) and methanol (25 ml) was stirred for 1 hour at 0° C. and then at room temperature for 3 days, the precipitate was collected and dissolved in water, and this solution was acidified with 2N HCl and extracted with ethyl acetate (2×30 ml). The combined extracts were washed with brine (30 ml), dried over sodium sulfate and concentrated in vacuo, leaving the free acid form of title product (0.4 g, 29%) as a yellow solid. The latter was converted to sodium salt according to the method of Example 42.

EXAMPLE 75

Sodium Salt of 5-[4-(2-Phenoxy-1-hydroxyethyl)benzyl]thiazolidine-2,4-dione

Title product of Preparation 32 (1.5 g) was stirred in THF (50 ml) and 3.5% $HClO_4$ (30 ml) at room temperature for 18 hours. The solution was extracted with ethyl acetate, and the extracts washed with saturated NaCl, dried ($MgSO_4$) and solvent removed in vacuo. The residue was purified on silica gel using 1:1 hexane:ethyl acetate as eluant to afford 1.0 gram of the free acid form of title product as an oil. The sodium salt was prepared by combining the latter with a molar equivalent of $NaOCH_3$ in $CH_3OH$, and evaporation; m.p. 85°–90° C.

EXAMPLE 76

5-[4-(2-Phenoxyacetyl)benzyl]thiazolidine-2,4-dione

Title product of the preceding Example (1.0 mmol, 343 mg) was dissolved in ether (10 ml) at 0° C. Jones' Reagent (1.5 ml) was added and the solution stirred for 1 hour. The mixture was diluted with ether, washed with $H_2O$, saturated NaCl, dried ($MgSO_4$) and the solvent removed in vacuo to afford present title product as a solid; m.p. 170°–174° C.

Analysis calculated for $C_{18}H_{15}O_4NS$: C, 63.33; H, 4.43; N, 4.10%. Found: C, 62.89; H, 4.70; N, 4.17%.

PREPARATION 1

4-(Bromomethyl)benzenesulfonyl Chloride p-Toluenesulfonyl chloride (0.52 mol, 100 g), N-bromosuccinimide (0.62 mol, 110.3 g), and benzoyl peroxide (5 g) were heated to reflux in carbon tetrachloride (500 ml) for 1 hour. The mixture was filtered and the filtrate was concentrated in vacuo. The residue was triturated with isopropyl ether to afford 40.1 g of title product as a white solid; m.p. 70°–73° C.

PREPARATION 2

N-Benzyl-N-methyl-4-(bromomethyl)benzenesulfonamide

The title product of the preceding Preparation (37 mmol, 9.9 g) was dissolved in methylene chloride (150 ml) at room temperature. Benzylmethylamine (74 mmol, 9.0 g) dissolved in methylene chloride (25 ml) was added dropwise over 20 minutes and the reaction mixture was stirred for 1 hour. The solution was with water (2×100 ml), saturated sodium chloride (100 ml), dried ($Na_2SO_4$) and the solvent removed in vacuo. The residue was recrystallized from ethyl acetate to afford 7.1 g of the title sulfonamide; m.p. 122°–123° C.

Analysis calculated for $C_{15}H_{16}O_2NSBr$: C, 50.85; H, 4.55; N, 3.95%. Found: C, 50.91; H, 4.60; N, 3.93%.

PREPARATION 3

N-Methyl-N-(2-phenylethyl)-4-(bromomethyl)benzenesulfonamide

Using a molar equivalent amount of N-methylphenethylamine in place of the benzylmethylamine, the method of the preceding Preparation was used to convert the sulfonyl chloride of Preparation 1 to present title product, isolated as a gum.

PREPARATION 4

5-(Phenylmethylene)thiazolidine-2,4-dione

Benzaldehyde (0.78 mol, 82.8 g) and 2,4-thiazolidinedione (0.85 mol, 100 g) were heated to reflux in a mixture of pyridine (215 ml) and dimethylformamide (400 ml) for 18 hours. The reaction mixture was cooled to 55° C. and diluted with hexane (360 ml) and water (900 ml) and stirred for 1 hour after cooling to room temperature. The product was collected to afford 175 g of pale yellow solid; m.p. 246°–248° C.

PREPARATION 5

5-Benzylthiazolidine-2,4-dione

The title product of the preceding Preparation (0.12 mol, 25 g) was hydrogenated in a Paar shaker at 50 psig for 18 hours at room temperature using 10% Pd/C (25 g of 50 wt % $H_2O$) in tetrahydrofuran (750 ml) and acetic acid (250 ml). The catalyst was removed by filtration and the solvent removed in vacuo. The crude solid was recrystallized from ethanol:water (1:2) to afford 15.4 g of pale grey crystals; m.p. 101°–103° C.

Analysis calculated for $C_{10}H_9O_2NS$: C, 57.95; H, 4.38; N, 6.76%. Found: C, 57.95; H, 4.30; N, 6.76%.

PREPARATION 6

4-[(Thiazolidine-2,4-dion-5-yl)methyl]benzenesulfonyl Chloride

Chlorosulfonic acid (5 ml) was cooled to 0° C. and the 5-benzyl-2,4-thiazolidinedione prepared above (9.6 mmol, 2.0 g) was added portionwise. The reaction mixture was stirred at room temperature for 0.5 hour and poured into ice (25 g). The solution was extracted with methylene chloride (2×50 ml) and the organic layers were dried ($Na_2SO_4$) and solvent removed in vacuo to afford title product which was used without further purification.

PREPARATION 7

4-(2-Phenylethylthio)benzaldehyde

A mixture of 2-phenylethylmercaptan (72.3 mmol, 10.0 g), 4-bromobenzaldehyde (79.6 mmol, 14.7 g) and potassium carbonate (116 mmol, 16 g) were stirred in dimethylformamide (100 ml) at 110° C. for 48 hours. The solution was cooled and diluted with water (200 ml). The aqueous was extracted with ether (3×200 ml) and the combined ether layers were dried ($Na_2SO_4$) and concentrated in vacuo. The residue was purified on silica gel using hexane:ethyl acetate (9:1) as eluant to afford 11.7 g (67%) of present title product as a yellow oil.

$^1$H-NMR($CDCl_3$)delta(ppm): 3.1 (d of t), 7.2 (s), 7.3 (d), 7.7 (d), 9.9 (s). MS (m+) 242.

PREPARATION 8

4-(2-Phenylethylthio)acetophenone

A mixture of 2-phenylethylmercaptan (0.173 mol, 24 g), 4-bromoacetophenone (0.19 mol, 38 g) and potassium carbonate (0.27 mol, 37 g) were heated in dimethylformamide (50 ml) at 110° C. for 24 hours. The reaction mixture was cooled and diluted with water (500 ml). The solution was extracted with ether (300 ml) and the ether was washed with water (2×150 ml). The ether was dried ($Na_2SO_4$) and removed in vacuo. The crude product was purified on silica gel using hexane:ethyl acetate (20:1) as eluant to afford 22.5 g of title product as an oil.

PREPARATION 9

4-[2-(4-Chlorophenyl)ethylthio]benzaldehyde

Title product was prepared from 2-(4-chlorophenyl)ethyl mercaptan and 4-bromobenzaldehyde according to the method of Preparation 7.

PREPARATION 10

4-(Benzylthio)benzaldehyde

Title product was prepared from benzyl mercaptan (145 mmol, 17.9 g) and 4-bromobenzaldehyde according to the method of Preparation 1 yielding 4 g of purified product following chromatography on silica gel using 9:1 hexane:ethyl acetate as eluant.

PREPARATION 11

4-(3-Phenylpropylthio)benzaldehyde

By the method of Preparation 7, 3-phenylpropyl mercaptan (41.1 g) and 4-bromobenzaldehyde (53.7 g) were converted to 70 g of present title product, isolated as an oil following chromatography on silica gel using 9:1 hexane:ethyl acetate as eluant; tlc Rf 0.4 (1:4 ethyl acetate:hexane).

PREPARATION 12

4-(2-Bromoethyl)benzaldehyde

To a solution of (2-bromoethyl)benzene (100 mmol, 18.5 g) in methylene chloride (185 ml) at 0° C. was added dropwise titanium tetrachloride (200 mmol, 22 ml). The mixture was stirred for 10 minutes and alpha,alpha-dichloromethyl methyl ether (100 mmol, 9 ml) was added dropwise. The reaction mixture was stirred at room temperature for 1 hour and poured into saturated NaHCO$_3$ (1 liter). Ethyl acetate (750 ml) was added and the solution was filtered through diatomaceous earth, the organic layer separated, dried (Na$_2$SO$_4$) and solvent removed in vacuo. The residue was triturated with hexane to afford 8.7 g of title product; m.p. 49°–52° C.

PREPARATION 13

4-[2-(Phenylthio)ethyl]benzaldehyde

Sodium hydride (31.1 mmol, 1.5 g of 50% dispersion in oil) was added to dimethylformamide (15 ml) at room temperature. Benzenethiol (29.6 mmol, 3.3 g) was added (exothermic) and the mixture was stirred for 15 minutes. The aldehyde of the preceding Preparation (29.6 mmol, 6.3 g) dissolved in dimethylformamide (15 ml) was added dropwise and the reaction mixture was heated at 110° C. for 18 hours. The solution was cooled, diluted with water (75 ml) and extracted with ether. The ether was washed with water (2×75 ml, 1N NaOH (2×50 ml), water (2×50 ml), and saturated NaCl (50 ml), dried (Na$_2$SO$_4$) and removed in vacuo. The crude oil was purified on silica gel using hexane:ethyl acetate (9:1) to afford 5.1 g of title product as a yellow oil; tlc Rf 0.33 (1:5 ethyl acetate:hexane).

PREPARATION 14

4-(Diethoxymethyl)benzyl Alcohol

To a solution of terephthalaldehyde mono(diethyl acetal) (1.9 ml, 9.6 mmol) in methanol (35 ml) was added sodium borohydride (1.1 g, 28.8 mmol) while cooling. After 5 minutes at room temperature the reaction was quenched with water (50 ml) and the mixture was extracted with ethyl acetate (2×50 ml). The combined extracts were washed with water and brine, dried over sodium sulfate and concentrated in vacuo, leaving title product as a colorless oil (1.81 g, 90%).

PREPARATION 15

1-(Methoxymethyl)-4-(diethoxymethyl)benzene

To title product of the preceding Preparation (1.51 g, 7.2 mmol) in dry THF (5 ml) at 0° C. was added potassium tert-butoxide (1.21 g, 11 mmol) and after 5 minutes iodomethane (0.89 ml, 14 mmol). The solution was stirred at room temperature for 1 hour, then diluted with water (15 ml) and extracted with ether (2×10 ml). The combined organic layers were washed with water (10 ml), brine (10 ml), dried over sodium sulfate and concentrated in vacuo, leaving present title product (1.43 g, 89%) as a colorless oil.

PREPARATION 16

4-(Methoxymethyl)benzaldehyde

A solution of title product of the preceding Preparation (1.3 g, 5.8 mmol) in THF (12.5 ml) and 1N HCl (15 ml) was stirred at room temperature for 2 hours. Water (10 ml) was added and the mixture was extracted with chloroform (2×15 ml). The combined extracts were washed with water (15 ml) and brine (15 ml), dried over sodium sulfate and concentrated in vacuo, leaving present title product (0.81 g, 93%) as a light yellow oil.

PREPARATION 17

4-[3-(3-Methoxyphenyl)-2-propenoyl]aniline

A solution of p-aminoacetophenone (14.9 g, 0.11 mol) and m-anisaldehyde (10.0 g, 73 mmol) in methanol (500 ml) and 1N NaOH (260 ml) was stirred at room temperature overnight. The precipitate was collected, the filtrate was concentrated to 300 ml and the new precipitate was collected. The combined solids were recrystallized from isopropanol to give present title product as a yellow solid (10.4 g, 56%).

PREPARATION 18

4-[3-(3-Methoxyphenyl)propionyl]aniline

A solution of title product of the preceding Preparation (3.9 g, 15 mmol) in ethanol (100 ml) containing 10% palladium on carbon (0.40 g) was hydrogenated in a Parr shaker at 50 psig. The solution was filtered and the filtrate was concentrated in vacuo. The product was dissolved in ethyl acetate (150 ml) and this solution was washed with 1N HCl (2×75 ml), water (75 ml) and brine (75 ml), dried over sodium sulfate and concentrated in vacuo, leaving present title product (2.1 g, 53%) as an oily solid.

PREPARATION 19

3-[4-[3-(3-Methoxyphenyl)propionyl]phenyl]-2-bromopropionic Acid

To an ice-cooled solution of title product of the preceding Preparation (1.0 g, 3.9 mmol) in acetone (30 ml) and 48% HBr (2 ml) was added a solution of sodium nitrite (0.27 g, 3.9 mmol) in water (2 ml). After 5 minutes acrylic acid (4 ml, 58 mmol) was added, followed after another 5 minutes by copper (I) bromide (5 mg). The solution was stirred for 20 minutes at room temperature, then diluted with water (30 ml), concentrated to 30 ml and extracted with ethyl acetate (2×20 ml). The combined extracts were washed with water (20 ml) and brine (20 ml), dried over sodium sulfate and concentrated in vacuo to leave present title product as a dark liquid.

PREPARATION 20

Methyl 4-(Dimethoxymethyl)benzoate

Methyl 4-formyl-benzoate (10.0 g, 60.9 mmol) was dissolved in a solution of methanol (100 ml) and trimethyl orthoformate (5 ml). p-Toluenesulfonic acid (100 mg) was added and the solution was refluxed overnight. After cooling to room temperature, the reaction was quenched by the addition of triethylamine (0.5 ml) and then poured into 5% aqueous NaHCO$_3$ (100 ml). The aqueous layer was extracted with ether (3×100 ml) and the combined organic solutions were dried (MgSO$_4$) and concentrated to give the methyl acetal ester (12.24 g, 96%). The material crystallized upon standing (m.p. 28°–30° C.).

PREPARATION 21

Methyl 5-(Dimethoxymethyl)pyridine-2-carboxylate

To a solution of methyl 5-(dibromomethyl)pyridine-2-carboxylate (927 mg, 3.00 mmol) in methanol (10 ml) and trimethyl orthoformate (2 ml) was added a solution AgNO$_3$ (1.12 g, 6.6 mmol) in methanol (20 ml) over 15 minutes. After refluxing the reaction for 1 hour, it was cooled and poured into a solution of NaHCO$_3$ (0.84 g, 10 mmol) in water (50 ml) containing a small amount of NaCl. The thick slurry was filtered through a 25–50 micron frit, and the filtrate concentrated to 10 ml and extracted with ethyl acetate (3×10 ml). The combined organic layers were dried (MgSO$_4$), filtered and concentrated to give title product (550 mg, 96%).

PREPARATION 22

Methyl 2-(Dimethoxymethyl)pyridine-5-carboxylate

To a solution of methyl 2-formylpyridine-5-carboxylate (2.00 g, 12.1 mmol) in methanol (20 ml) and trimethyl orthoformate (5 ml) was added H$_2$SO$_4$ (conc., 1.5 ml). After refluxing overnight, the reaction was cooled and concentrated to a thick slurry and then poured into saturated NaHCO$_3$ (50 ml). The latter was extracted with ether (3×30 ml) and the combined organic layers dried (MgSO$_4$) and concentrated to afford title product (1.91 g, 75%).

PREPARATION 23

4-(4-Phenylbutyryl)benzaldehyde

To THF (30 ml) at −10° C. was added diisopropylamine (8.01 ml, 57.1 mmol) followed by the dropwise addition of n-butyl lithium (2.0M in hexane, 28.6 ml, 57.2 mmol) at a rate such that the internal temperature was kept less than −5° C. A solution of 4-phenylbutyric acid (4.70 g, 28.6 mmol) in THF (20 ml) was then added over 5 minutes followed by hexamethylphosphoramide (4.98 ml, 26.8 mmol). After stirring for 30 minutes at room temperature, the reaction mixture was cooled to −10° C. and a solution of title product of Preparation 20 (5.0 g, 23.8 mmol) in THF (20 ml) was added dropwise. After stirring at room temperature for 1 hour, the reaction was quenched into an equal volume of 3N HCl and stirred for an additional hour. After neutralization to pH 8 with NaHCO$_3$, it was extracted with ether (3×50 ml) and the combined organic layers were washed with water (50 ml), dried (MgSO$_4$) and concentrated to afford 3.95 g of a yellow oil. Chromatography on silica gel with 3:1 hexane:ethyl acetate gave 2.57 g of a white solid containing the desired title product and methyl 4-formylbenzoate.

PREPARATION 24

2-(3-Phenylpropionyl)pyridine-5-carbaldehyde

By the method of the preceding Preparation, 3-phenylpropionic acid and the title product of Preparation 21 were converted to present title product in 19% yield.

PREPARATION 25

5-(3-Phenylpropionyl)pyridine-2-carbaldehyde

By the method of Preparation 23, 3-phenylpropionic acid and the title product of Preparation 22 were converted to present title product in 26% yield.

PREPARATION 26

2-(4-Diethoxymethylphenyl)ethanol

To a solution of 4-(diethoxymethyl)benzaldehyde (5.0 g, 24 mmol) in ether (65 ml), cooled to −10° C., was added dropwise a 1.5M toluene-THF methylmagnesium bromide solution (64 ml, 96 mmol) at such a rate that the temperature remains below 0° C. After the addition the reaction was quenched with saturated ammonium chloride (80 ml) and the solution was diluted with water (50 ml) and extracted with ether (2×75 ml). The combined extracts were washed with water (50 ml) and brine (50 ml), dried over sodium sulfate and concentrated in vacuo, leaving present title product (5.2 g, 97%) as an oil.

PREPARATION 27

4-(1-Hydroxyethyl)benzaldehyde

Title product of the preceding Preparation (5.2 g, 23 mmol) in THF (30 ml) and 1N HCl (30 ml) was stirred at room temperature for 2 hours, then diluted with water (30 ml) and extracted with chloroform (2×50 ml). The combined extracts were washed with brine (30 ml), dried over sodium sulfate and concentrated in vacuo, leaving present title product (3.2 g, 92%) as an oil.

PREPARATION 28

5-[4-(1-Hydroxyethyl)phenylmethylene]thiazolidine-2,4-dione

Title product of the preceding Example (3.2 g, 21 mmol) was combined with 2,4-thiazolidinedione (3.6 g, 31 mmol) and sodium acetate (5.1 g, 62 mmol) and heated to 140° C. for 1 hour. The yellow solid was triturated with water for 30 minutes, then filtered and dried to yield present title product (4.3 g, 81%).

PREPARATION 29

5-(4-Acetylphenylmethylene)thiazolidine-2,4-dione

Title product of the preceding Preparation (3.5 g, 14 mmol) in acetone (100 ml), cooled to 0° C., was added dropwise to a 2.67M solution of Jones' Reagent (10.5 ml, 28 mmol) over 10 minutes. The solution was stirred for 2 hours at room temperature, then diluted with water (100 ml) and extracted with ethyl acetate (3×60 ml). The combined extracts were washed with water (2×60 ml) and brine (60 ml), dried over sodium sulfate and concentrated in vacuo, leaving present title product (3.1 g, 88%) as a yellow solid.

PREPARATION 30 alpha-Phenoxymethyl-4-benzyl Alcohol

Phenol (15.0 mmol, 1.41 g), alpha,4-dibromoacetophenone (15.0 mmol, 4.2 g) and potassium carbonate (30.0 mmol, 4.15 g) were heated to reflux in acetone (50 ml) for 8 hours. The solution was cooled, concentrated, diluted with water (50 ml) and extracted with ether (2×100 ml). The ether layers were combined, washed with 10% NaOH (50 ml) and then saturated NaCl (50 ml), dried (MgSO4) to afford a mixture of title product alpha-phenoxymethyl-4-benzyl alcohol and unreacted dibromoacetophenone, all of which was dissolved in CH2Cl2 (25 ml) and isopropanol (25 ml) and cooled to 0° C. Sodium borohydride (15.0 mmol, 570 mg) was added and the mixture was stirred for 1 hour. Water (50 ml) was added and extracted with methylene chloride. The organics were washed with saturated NaCl, dried (MgSO4) and evaporated. The residue was purified on silica gel using 1:1 hexane:methylene chloride as eluant to afford 3.0 g of present title product as an oil.

PREPARATION 31

4-(2-Phenoxy-1-(dimethyl-t-butylsilyloxy)ethyl)phenyl Bromide

Title product of the preceding Preparation (10.0 mmol, 2.93 g), t-butyldimethylsilyl chloride (12.5 mmol, 1.9 g), and imidazole (25 mmol, 1.7 g) were stirred in DMF (40 ml) at room temperature for 36 hours. 10% NaHCO3 (150 ml) was added and the solution was extracted with hexane (2×200 ml) and the organics were washed with water, saturated NaCl, dried (MgSO4) and evaporated. The product was purified on silica gel using hexane:butyl chloride 4:1 as eluant to afford 2.5 g of present title product as a colorless oil.

PREPARATION 32

5-[4-(2-Phenoxy-1-(dimethyl-t-butylsilyloxy)ethyl)benzyl]thiazolidine-2,4-dione Title product of the preceding Preparation (6.1 mmol, 2.5 g) was dissolved in THF (50 ml) and cooled to −78° C. n-Butyllithium (6.7 mmol in hexane) was added and the mixture stirred for 45 minutes. DMF (6.7 mmol, 0.52 ml) was added and the mixture was stirred at −78° C. for 1 hour, following which 10% HCl (25 ml) was added and the mixture was warmed to room temperature and extracted with ethyl acetate. The organics were dried (MgSO4) and evaporated in vacuo to afford intermediate 4-(2-phenoxy-1-(dimethyl-t-butylsilyloxy)-benzaldehyde, all of which was intimately mixed with thiazolidine-2,4-dione (8.0 mmol) and sodium acetate (15.0 mmol, 1.73 g) and the mixture fused at 160° C. for 1 hour, then cooled to room temperature. The solids were dissolved in ethyl acetate (400 ml) and CH3OH (25 ml), and washed with water and then saturated NaCl, dried (MgSO4) and evaporated to afford intermediate 5-[4-(2-phenoxy-1-(dimethyl-t-butylsilyloxy)ethyl)-phenylmethylene]thiazolidine-2,4-dione. The latter was dissolved in CH3OH (100 ml) and stirred with 3.5% Na/Hg (20 g) for 2 hours. The solids were removed by filtration over diatomaceous earth and the solvent concentrated. The residue was dissolved in ethyl acetate, washed with cold 10% HCl and then saturated NaCl,
dried (MgSO4) and evaporated. The residue was purified on silica gel using 2:1 hexane:ethyl acetate to afford 1.6 g of present title product as an oil.

PREPARATION 33

5-[(4-Acetylphenyl)methyl]thiazolidine-2,4-dione

A solution of 4-acetyl-alpha-bromobenzenepropanoic acid (87 g, 0.32 mol) and thiourea (48.7 g, 0.64 mol) in sulfolane (100 ml) was heated to 105°–110° C. for 5 hours. To this mixture was added a 2N HCl solution (162 ml) and the resulting solution was heated to 105°–110° C. overnight. After cooling and diluting with water, the solid was collected, washed with water and dried (75 g, 94%); m.p. 171°–172° C.

We claim:

1. A compound having the formula

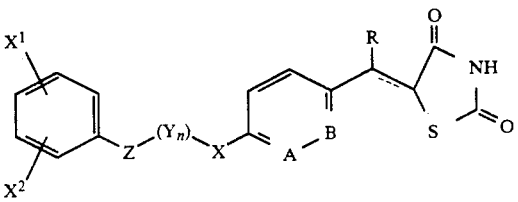

wherein
the dotted line represents a bond or no bond;
A and B are each CH;
X is S, SO, SO2, CHOH or CO;
n is 0 or 1;
Y is CHR$^1$ or NR$^2$, with the proviso that when n is 1 and Y is NR$^2$, X is SO2 or CO;
Z is

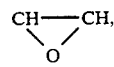

OCH2, SCH2, SOCH2 or SO2CH2;
R, R$^1$, R$^2$ and R$^3$ are each independently hydrogen or methyl; and
X$^1$ and X$^2$ are each independently hydrogen, methyl, trifluoromethyl, phenyl, benzyl, hydroxy, methoxy, phenoxy, benzyloxy, bromo, chloro or fluoro; a pharmaceutically-acceptable cationic salt thereof; or a pharmaceutically-acceptable acid addition salt thereof.

2. A compound of claim 1 wherein the dotted line represents no bond, X is CO, n is O and R is hydrogen.

3. A pharmaceutical composition which comprises an effective blood glucose lowering amount of a compound of claim 1 and a pharmaceutically-acceptable carrier.

4. A method of lowering blood glucose in a hyperglycemic mammal which comprises administering to said mammal a blood glucose lowering effective amount of a compound of claim 1.

5. A pharmaceutical composition which comprises an effective blood cholesterol lowering amount of a compound of claim 1 and a pharmaceutically-acceptable carrier.

6. A method of lowering blood cholesterol in a hypercholesterolemic mammal which comprises administering to said mammal a blood cholesterol lowering effective amount of a compound of claim 1.

* * * * *